United States Patent [19]

Harada et al.

[11] Patent Number: 5,892,091
[45] Date of Patent: Apr. 6, 1999

[54] CATALYST FOR DECARBONYLATION REACTION

[75] Inventors: Katsumasa Harada; Yoichi Imbe; Keigo Nishihira; Shuji Tanaka; Satoru Fujitsu; Ryoji Sugise; Koichi Kashiwagi; Toshihiko Sumida; Takashi Doi; Masayuki Nishio, all of Yamaguchi, Japan

[73] Assignee: Ube Industries, Ltd., Yamaguchi, Japan

[21] Appl. No.: 889,390

[22] Filed: Jul. 8, 1997

Related U.S. Application Data

[63] Continuation-in-part of Ser. No. 627,897, Apr. 3, 1996, Pat. No. 5,648,510.

[30] Foreign Application Priority Data

| Apr. 4, 1995 | [JP] | Japan | 7-78766 |
| Aug. 30, 1996 | [JP] | Japan | 8-229632 |
| Oct. 4, 1996 | [JP] | Japan | 8-264766 |

[51] Int. Cl.$^6$ ................................ C07C 69/96
[52] U.S. Cl. ............ 558/270; 558/274; 558/280; 558/277; 558/282; 549/71; 549/484
[58] Field of Search .................. 558/280, 282, 558/277, 270, 274, 271; 549/71, 484

[56] References Cited

U.S. PATENT DOCUMENTS

| 4,515,978 | 5/1985 | Harris | 549/484 |
| 5,196,561 | 3/1993 | Mori | 558/277 |
| 5,214,182 | 5/1993 | Knifton | 558/277 |
| 5,274,164 | 12/1993 | Wettling | 558/282 |
| 5,424,473 | 6/1995 | Galvan | 558/270 |

OTHER PUBLICATIONS

CA: 108:150587 abst of "Preparation of difluoro-phophononoacetic acid and its derivatives", Burton, J Org Chem, 53(7), pp. 1523–1527, 1988.

CA: 127:346520 abs of "New bis(ferrocenyl)–bearing tetraazaporphyrinogen as an electroactive ligand for ruthenium (II)", Chabert–Couchouron, New J. Chem 21(9) pp. 993–999, 1997.

CA: 125:168268 abs of "Ferrocenylpyrazole as building block for the design of new redox–active macrocycles", Marzin, An Quim INt Ed., 92(2) pp. 70–78, 1996.

CA: 75:139987 abs of "Orientation in heterolytic addition to alpha haloacrylates", Dyatkin, Doki Akad Nauk SSSR, 199(5), pp. 1066–1069, 1971.

*Primary Examiner*—Gary Geist
*Assistant Examiner*—Jean F. Vollano
*Attorney, Agent, or Firm*—McAulay Nissen Goldberg Kiel & Hand, LLP

[57] ABSTRACT

A catalyst composed of an organic phosphorus compound having a trivalent or pentavalent phosphorus atom and at least one carbon-phosphorus bonding or a combination of the organic phosphorus compound and a halogen atom-containing compound is effective for decarbonylation, that is, for releasing carbon monoxide from a compound containing a moiety of —CO—CO—O— in its molecular structure.

12 Claims, No Drawings

CATALYST FOR DECARBONYLATION REACTION

This is a Continuation-in-Part of application of Ser. No. 08/627,897 filed Apr. 3, 1996, now U.S. Pat. No. 5,648,510 the content of which are hereby incorporated by reference.

FIELD OF THE INVENTION

The present invention relates to a catalyst for decarbonylation reaction. The invention also relates to a process for releasing carbon monoxide from a compound containing a moiety of —CO—CO—O— in its molecular structure. Particularly, the invention relates to a process for releasing or eliminating carbon monoxide from a compound containing a moiety of —CO—CO—O— in its molecular structure to prepare an aryl ester of a haloformic acid, an aryl or alkyl ester of an aromatic carboxylic acid, an aryl ester of a heterocyclic carboxylic acid, or a diaryl or dialkyl ester of a carbonic acid.

BACKGROUND OF THE INVENTION

DE 2,131,555, DE 3,000,524 and U.S. Pat. No. 5,324,473 describe that an aryl ester of a haloformic acid, i.e., an aryl haloformate, can be prepared by a process in which phosgene and an aromatic hydroxyl compound are caused to react in the presence of such a catalyst as an amine derivative or a phosphorus compound. This process has disadvantages in that the toxic phosgene is necessarily employed and a great amount of an alkali is used.

It is known that an aryl ester of an aromatic carboxylic acid such as aryl benzoate can be prepared by reacting phenol with an aromatic carboxylic acid or an aromatic carboxylic acid chloride.

The diaryl carbonate is heretofore prepared by causing a reaction between phosgene and an aromatic hydroxyl compound in the presence of an alkali (see Japanese Patent Provisional Publication No. 62(1987)-190146). This process has disadvantages in that the toxic phosgene is necessarily employed and a great amount of an alkali is used.

The diaryl carbonate is also prepared by a process which comprises transesterification between a dialkyl carbonate and an aromatic hydroxy compound in the presence of a catalyst (see Japanese Patent Publications No. 56(1981)-42577 and H1(1989)-5588). This transesterification process, however, also has a disadvantage in that its reaction rate is not high even if a highly active catalyst is employed. This means that a large scaled apparatus is required when a diaryl carbonate is produced in an industrially applicable scale.

Yuki Gosei Kagaku (Organic Synthetic Chemistry in Japan), 5, Report 47, pp. 70–71(1948) teaches a reaction in which diphenyl oxalate is heated to release carbon monoxide to give diphenyl carbonate. This report does not mention with respect to the yield and selectivity of the reaction. According to a trace experiment of the experiment set forth in this report, only a small amount of diphenyl carbonate is produced.

U.S. Pat. No. 4,544,507 describes that the carbonic acid dialkyl ester, i.e., dialkyl carbonate, can be prepared by heating a dialkyl oxalate in a liquid phase at 50°–150° C. in the presence of an alcolate catalyst. In the working example of the Patent, a diphenyl oxalate is heated in the presence of a potassium phenoxide catalyst only to give mainly the diphenyl oxalate, namely, the starting compound.

SUMMARY OF THE INVENTION

It is a principal object of the present invention to provide a new catalyst for decarbonylation.

It is another object to provide a process for removing carbon monoxide from a compound containing a moiety of —CO—CO—O— in its molecular structure.

The present invention resides in a process for releasing or eliminating carbon monoxide from a compound containing a moiety of —CO—CO—O— in its molecular structure which comprises heating the compound in the presence of an organic phosphorus compound having a trivalent or pentavalent phosphorus atom and at least one carbon-phosphorus bonding.

The invention also resides in a process for removing carbon monoxide from a compound containing a moiety of —CO—CO—O— in its molecular structure which comprises heating the compound in the presence of an organic phosphorus compound having a trivalent or pentavalent phosphorus atom and at least one carbon-phosphorus bonding and a halogen atom-containing compound.

The invention further resides in a catalyst for decarbonylation of a compound containing a moiety of —CO—CO—O— in its molecular structure, which comprises an organic phosphorus compound having a trivalent or pentavalent phosphorus atom and at least one carbon-phosphorus bonding.

The invention furthermore resides in a catalyst for decarbonylation of a compound containing a moiety of —CO—CO—O— in its molecular structure, which comprises an organic phosphorus compound having a trivalent or pentavalent phosphorus atom and at least one carbon-phosphorus bonding and a halogen atom-containing compound.

In the above-mentioned processes, the organic phosphorus compound preferably is a phosphonium salt, a phosphine, a phosphine dihalide or a phosphine oxide, more preferably is a tetraarylphosphonium salt, a triarylphosphine, a triarylphosphine dihalide, or a triarylphosphine oxide, and specifically preferably is a tetraarylphosphonium halide, a tetraarylphosphonium hydrogen dihalide, or a triarylphosphine dihalide.

The compound containing a moiety of —CO—CO—O— preferably has the formula:

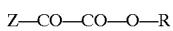

Z—CO—CO—O—R in which Z is an aryl group, a halogen atom, a heterocyclic group, an aryloxy group, or an alkoxy group, and R is an aryl group or an alkyl group.

The halogen atom-containing compound preferably is an organic or inorganic halide compound, more preferably is a compound selected from the group consisting of halides of aluminum, halides of metals belonging to the platinum group, halides of phosphorus, hydrogen halides, halides of sulfur, and halogens, and specifically preferably is an organic compound having a C—Hal bonding, Hal meaning a halogen atom, a C—Si—Hal bonding, a —C(O)—Hal bonding, or a C—S(O)$_2$—Hal bonding. Most preferred is a chlorine atom-containing compound.

DETAILED DESCRIPTION OF THE INVENTION

The decarbonylation catalyst of the invention can be employed in a variety of decarbonylation reactions for releasing or eliminating carbon monoxide from a compound containing a moiety of —CO—CO—O— in its molecular structure. The compound containing a moiety of —CO—CO—O— preferably has a general formula:

Z—CO—CO—O—R in which Z is an aryl group, a halogen atom, a heterocyclic group, an aryloxy group, or an alkoxy group, and R is an aryl group or an alkyl group.

The aryl group for Z preferably is an unsubstituted phenyl group; a phenyl group substituted with, for instance, an alkyl group of 1–12 carbon atoms (e.g., methyl or ethyl), an alkoxy group of 1–12 carbon atoms (e.g., methoxy or ethoxy), a halogen atom (e.g., fluorine or chlorine), or a nitro group; an unsubstituted naphthyl group; or a naphthyl group substituted with, for instance, one of the above-mentioned substituents. Examples of the substituted phenyl groups include various isomers such as 2-(or 3-, or 4-)alkylphenyl, e.g., 2-(or 3-, or 4-)methylphenyl, or 2-(or 3-, or 4-)ethylphenyl; 2-(or 3-, or 4-)alkoxyphenyl, e.g., 2-(or 3-, or 4-)methoxyphenyl, or 2-(or 3-, or 4-)ethoxyphenyl; 2-(or 3-, or 4-)halogenated phenyl, e.g., 2- (or 3-, or 4-)fluorophenyl, or 2-(or 3-, or 4-)chlorophenyl; and 2-(or 3-, or 4-)nitrophenyl.

The halogen atom for Z preferably is fluorine, chlorine, or bromine.

The heterocyclic group for Z preferably is 2-thienyl or 2-furyl.

The aryloxy group for Z preferably is an unsubstituted phenoxy group; a phenoxy group substituted with, for instance, an alkyl group of 1–12 carbon atoms (e.g., methyl or ethyl), an alkoxy group of 1–12 carbon atoms (e.g., methoxy or ethoxy), a halogen atom (e.g., fluorine or chlorine), or a nitro group; an unsubstituted naphthoxy group; or a naphthoxy group substituted with, for instance, one of the above-mentioned substituents. Examples of the substituted phenoxy groups include various isomers such as 2-(or 3-, or 4-)alkylphenoxy, e.g., 2-(or 3-, or 4-)methylphenoxy, or 2-(or 3-, or 4-)ethylphenoxy; 2-(or 3-, or 4-)alkoxyphenoxy, e.g., 2-(or 3-, or 4-)methoxyphenoxy, or 2-(or 3-, or 4-)ethoxyphenoxy; 2-(or 3-, or 4-)halogenated phenoxy, e.g., 2- (or 3-, or 4-)fluorophenoxy, or 2-(or 3-, or 4-)chlorophenoxy; and 2-(or 3-, or 4-)nitrophenoxy.

The alkoxy group for Z preferably is an alkoxy group having 1 to 20 carbon atoms, and more preferably is an alkoxy group having 1 to 4 carbon atoms such as methoxy, ethoxy, n-(or iso-)propoxy, or n-(or iso-, or sec-, or tert-)butoxy.

An aryl group for R preferably is an unsubstituted phenyl group or a phenyl group substituted with, for instance, an alkyl group of 1–4 carbon atoms, an alkoxy group of 1–4 carbon atoms, a halogen atom, or a nitro group.

The alkyl group for R preferably is an alkyl group having 1 to 20 carbon atoms, and more preferably is an alkyl group having 1 to 4 carbon atoms such as methyl, ethyl, n-(or iso-)propyl, or n-(or iso-, or sec-, or tert-)butyl.

Examples of the decarbonylation reactions which can proceed in the presence of the decarbonylation catalyst of the invention include:

1) Decarboxylation of a diaryl oxalate to prepare a diaryl carbonate;
2) Decarbonylation of an aryl haloglyoxylate to prepare an aryl haloformate;
3) Decarbonylation of an aryl arylglyoxylate to give an aryl ester of an aromatic carboxylic acid; and
4) Decarbonylation of a dialkyl oxalate to prepare a dialkyl carbonate.

The decarbonylation process for preparing a diaryl carbonate from a diaryl oxalate can be illustrated as follows:

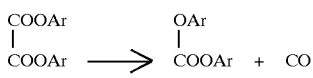

wherein Ar stands for an unsubstituted or substituted aryl group.

The aryl group of diaryl oxalate can be a phenyl or naphthyl group which can be substituted with an alkyl group of 1–12 carbon atoms (e.g., methyl or ethyl), an alkoxy group of 1–12 carbon atoms (e.g., methoxy or ethoxy), a halogen atom (e.g., fluorine or chlorine), or other substituent groups such as nitro. One or more substituent groups can be attached to any position of the aryl group. Accordingly, any isomers can be included. Examples of the substituted aryl groups include o-(or m-, or p-)methylphenyl, o-(or m-, or p-)ethylphenyl, o-(or m-, or p-)methoxyphenyl, o-(or m-, or p-)ethoxyphenyl, o-(or m-, or p-)fluorophenyl, o-(or m-, or p-)chlorophenyl, and o-(or m-, or p-)nitrophenyl.

In the decarbonylation processes of the invention, the organic phosphorus compound has a trivalent or pentavalent phosphorus atom, and has at least one carbon-phosphorus bonding. Preferred are organic phosphorus compounds having three or more carbon-phosphorus bondings. Preferred organic phosphorus compounds are a phosphonium salt having the following formula (A), a phosphine having the following formula (B), a phosphine dihalide having the following formula (C), and a phosphine oxide having the following formula (D):

Formula (A):
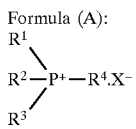

Formula (B):
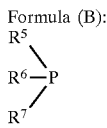

Formula (C):
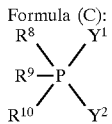

Formula (D):
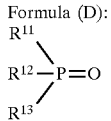

In the above-described formulas, each of $R^1$, $R^2$, $R^3$, $R^4$, $R^5$, $R^6$, $R^7$, $R^8$, $R^9$, $R^{10}$, $R^{11}$, $R^{12}$, and $R^{13}$ independently represents an aryl group of 6 to 10 carbon atoms, an alkyl group of 1 to 16 carbon atoms, an aralkyl group of 7 to 22 carbon atoms, an aryloxy group of 6 to 10 carbon atoms, or a heterocyclic group of 4 to 16 carbon atoms, X represents a counter ion of the phosphonium ion, and each of $Y^1$ and $Y^2$ represents a halogen atom.

Detailed descriptions are given below for the phosphonium salt of formula (A), the phosphine of formula (B), the phosphine dihalide of formula (C), and the phosphine oxide of formula (D).

(A) Phosphonium Salt

Formula (A):

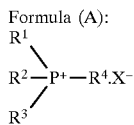

The phosphonium salt can be represented by the above formula (A), wherein each of $R^1$, $R^2$, $R^3$ and $R^4$ independently represents an aryl group of 6 to 10 carbon atoms, an alkyl group of 1 to 16 carbon atoms, an aralkyl group of 7 to 22 carbon atoms, an aryloxy group of 6 to 10 carbon atoms, or a heterocyclic group of 4 to 16 carbon atoms, and X represents a counter ion of the phosphonium ion. Any two of $R^1$, $R^2$, $R^3$ and $R^4$ may be combined to form a ring having the phosphorus atom as its ring member.

The aryl group is described in more detail. The aryl group can be a phenyl or naphthyl group. The phenyl or naphthyl group can have one or more substituents in any positions. Examples of the substituents include alkyl of 1 to 15 carbon atoms, preferably of 1 to 12 carbon atoms (e.g., methyl, ethyl, n-propyl, isopropyl, n-butyl, isobutyl, sec-butyl, or tert-butyl), alkoxy of 1 to 15 carbon atoms, preferably of 1 to 12 carbon atoms (e.g., methoxy, ethoxy, n-propoxy, isopropoxy, n-butoxy, isobutoxy, sec-butoxy, or tert-butoxy), alkoxycarbonyl of 2 to 12 carbon atoms, preferably of 2 to 8 carbon atoms (e.g., methoxycarbonyl or ethoxycarbonyl), aryl (e.g., phenyl), amino such as N,N-disubstituted amino (e.g., N,N-dimethylamino), cyano, nitro, and halo (e.g., fluoro, chloro, or bromo).

The alkyl group is described in more detail. The alkyl group can have 1 to 16 carbon atoms. Examples of the alkyl group include methyl, ethyl, n-propyl, isopropyl, n-butyl, isobutyl, sec-butyl, or tert-butyl. The alkyl group can have one or more substituents in any positions. Examples of the substituents are the same as those described for the substituents of the aryl group.

The aralkyl group is described in more detail. The aralkyl group can have 7 to 22 carbon atoms. Examples of the aralkyl group include benzyl, phenethyl and naphthylmethyl. The aralkyl group can have one or more substituents in any positions. Examples of the substituents are the same as those described for the substituents of the aryl group.

The aryloxy group is described in more detail. The aryloxy group can be a phenoxy or naphthoxy group. The aryloxy group can have one or more substituents in any positions. Examples of the substituents are the same as those described for the substituents of the aryl group.

The heterocyclic group is described in more detail. The heterocyclic group can have 4 to 16 carbon atoms, and at least one hetero atom such as oxygen, sulfur, or nitrogen. Examples of the heterocyclic group include thienyl, furyl, and pyridyl. The heterocyclic group can have one or more substituents in any positions. Examples of the substituents are the same as those described for the substituents of the aryl group.

The groups of $R^1$, $R^2$, $R^3$ and $R^4$ of the phosphonium salt can be the same or different from each other. For instance, all of the groups of $R^1$, $R^2$, $R^3$ and $R^4$ are aryl groups in one phosphonium salt, that is, a tetraarylphosphonium salt. Three of the groups are aryl groups and other one is another group, that is, a triarylphosphonium salt. Two of the groups are aryl groups and other two are other groups, that is, a diarylphosphonium salt. Only one of the groups is an aryl group and other three are other groups, that is, an arylphosphonium salt. All of the groups of $R^1$, $R^2$, $R^3$ and $R^4$ are other than the aryl groups. Preferred are the tetraarylphosphonium salt and an arylphosphonium salt in which three of the groups of $R^1$, $R^2$, $R^3$ and $R^4$ are aryl groups and other one is a heterocyclic group.

The counter ion ($X^-$) can be a halide ion (e.g., chloride ion, bromide ion, or iodide ion), a hydrogen dihalide ion (e.g., hydrogen dichloride ion, hydrogen dibromide ion, hydrogen diiodide ion, or hydrogen bromide chloride ion), a halogen acid ion (e.g., chlorate ion, bromate ion, or iodate ion), a per-halogen acid ion (e.g., perchlorate ion, perbromate ion, or periodate ion), an aliphatic carboxylate ion (e.g., acetate ion, trifluoroacetate ion, or propionate ion), an aromatic carboxylate ion (e.g., benzoate ion, or α- or β-naphthalenecarboxylate ion), an aromatic hydroxyl ion (e.g., phenoxide ion), an inorganic acid ion (e.g., sulfate ion, sulfite ion, phosphate ion, phosphite ion, borate ion, hydrogenborate ion, cyanate ion, thiocyanate ion, or fluoroborate ion), an alkylsulfonate or alkylsulfinate ion having an alkyl group of 1 to 16 carbon atoms (e.g., methyl, ethyl, n-propyl, or isopropyl), an arylsulfonate or arylsulfinate ion having an aryl group (e.g., phenyl, p-tolyl, or p-nitorophenyl), a tetraalkylborate ion having an alkyl group of 1 to 10 carbon atoms (e.g., tetramethylborate ion, or tetraethylborate ion), or a tetraarylborate ion (e.g., tetraphenylborate ion, or tetrakis-p-fluorophenylborate ion). Examples of preferred counter ions ($X^-$) include halide ions such as chloride ion, bromide ion and iodide ion, and hydrogen dihalide ions such as hydrogen dichloride ion, hydrogen dibromide ion, hydrogen diiodide ion, and hydrogen bromide chloride ion. Most preferred are chloride ion and hydrogen dichloride ion.

Concrete examples of the preferred phosphonium salts of the formula (A) are described below.

(1) Phosphonium salt in which all of $R^1$, $R^2$, $R^3$ and $R^4$ are aryl groups and $X^-$ is a halide ion Examples are tetraphenylphosphonium chloride, tetraphenylphosphonium bromide, tetraphenylphosphonium iodide, tetrakis(p-chlorophenyl)phosphonium chloride, tetrakis(p-fluorophenyl)phosphonium chloride, tetrakis (p-tolyl) phosphonium chloride, p-chlorophenyltriphenylphosphonium chloride, p-chlorophenyltriphenylphosphonium bromide, p-chlorophenyltriphenylphosphonium iodide, p-tolyltriphenylphosphonium chloride, p-tolyltriphenylphosphonium bromide, p-tolyltriphenylphosphonium iodide, m-trifluoromethylphenyltriphenylphosphonium chloride, p-biphenyltriphenylphosphonium chloride, m-methoxyphenyltriphenylphosphonium chloride, p-methoxyphenyltriphenylphosphonium chloride, p-ethoxyphenyltriphenylphosphonium chloride, p-ethoxyphenyltriphenylphosphonium bromide, p-ethoxyphenyltriphenylphosphonium iodide, p-dimethylaminophenyltriphenylphosphonium chloride, p-ethoxycarbonylphenyltriphenylphosphonium chloride, m-cyanophenyltriphenylphosphonium chloride, and 1-naphthyltriphenylphosphonium chloride. Most preferred is tetraphenylphosphonium chloride.

(2) Phosphonium salt in which all of $R^1$, $R^2$, $R^3$ and $R^4$ are aryl groups and $X^-$ is a hydrogen dihalide ion Examples are tetraphenylphosphonium hydrogen dichloride, tetraphenylphosphonium hydrogen dibromide, tetraphenylphosphonium hydrogen diiodide, and tetraphenylphosphonium hydrogen bromide chloride. Most preferred is tetraphenylphosphonium hydrogen dichloride.

(3) Phosphonium salt in which all of $R^1$, $R^2$, $R^3$ and $R^4$ are aryl groups and $X^-$ is an aliphatic or aromatic carboxylate ion Examples are tetraphenylphosphonium acetate, p-chlorophenyltriphenylphosphonium acetate, p-ethoxyphenyltriphenylphosphonium acetate, p-tolyltriphenylphosphonium acetate, tetraphenylphosphonium trifluoroacetate, and tetraphenylphosphonium benzoate.

(4) Phosphonium salt in which all of $R^1$, $R^2$, $R^3$ and $R^4$ are aryl groups and $X^-$ is fluoroborate ion Examples are tetraphenylphosphonium fluoroborate, p-chlorophenyltriphenylphosphonium fluoroborate, p-ethoxyphenyltriphenylphosphonium fluoroborate, and p-tolyltriphenylphosphonium fluoroborate.

(5) Phosphonium salt in which all of $R^1$, $R^2$, $R^3$ and $R^4$ are aryl groups and $X^-$ is thiocyanide ion An example is tetraphenylphosphonium thiocyanide.

(6) Phosphonium salt in which all of $R^1$, $R^2$, $R^3$ and $R^4$ are aryl groups and $X^-$ is an aromatic hydroxyl ion An example is tetraphenylphosphonium phenoxide.

(7) Phosphonium salt in which three of $R^1$, $R^2$, $R^3$ and $R^4$ are aryl groups, one is an alkyl group, and $X^-$ is a halide ion Examples are methyltriphenylphosphonium chloride, methyltriphenylphosphonium bromide, methyltriphenylphosphonium iodide, ethyltriphenylphosphonium chloride, ethyltriphenylphosphonium bromide, ethyltriphenylphosphonium iodide, n-propyltriphenylphosphonium chloride, n-propyltriphenylphosphonium bromide, n-propyltriphenylphosphonium iodide, isopropyltriphenylphosphonium chloride, isopropyltriphenylphosphonium bromide, n-dodecyltriphenylphosphonium chloride, n-dodecyltriphenylphosphonium bromide, chloromethyltriphenylphosphonium chloride, methyltris(m-chlorophenyl)phosphonium chloride, methyltris(m-chlorophenyl)phosphonium bromide, ethyltris(m-chlorophenyl)phosphonium chloride, and ethyltris(m-chlorophenyl)phosphonium bromide.

(8) Phosphonium salt in which three of $R^1$, $R^2$, $R^3$ and $R^4$ are aryl groups, one is an aralkyl group, and $X^-$ is a halide ion Examples are benzyltriphenylphosphonium chloride, p-fluorobenzyltriphenylphosphonium chloride, p-fluorobenzyltriphenylphosphonium bromide, 2,4-dichlorobenzyltriphenylphosphonium chloride, 2,4-dichlorobenzyltriphenylphosphonium bromide, p-n-butoxybenzyltriphenylphosphonium chloride, p-n-butoxybenzyltriphenylphosphonium bromide, 2-naphthylmethyltriphenylphosphonium chloride, 2-naphthylmethyltriphenylphosphonium bromide, 9-fluorenyltriphenylphosphonium chloride, and 9-fluorenyltriphenylphosphonium bromide.

(9) Phosphonium salt in which three of $R^1$, $R^2$, $R^3$ and $R^4$ are aryl groups, one is a heterocyclic group, and $X^-$ is a halide ion An example is 2-thiophenetriphenylphosphonium chloride.

(10) Phosphonium salt in which three of $R^1$, $R^2$, $R^3$ and $R^4$ are aryl groups, one is an aryloxy group, and $X^-$ is a halide ion An example is phenoxytriphenylphosphonium chloride.

(11) Phosphonium salt in which three of $R^1$, $R^2$, $R^3$ and $R^4$ are aryl groups, one is an alkyl group, and $X^-$ is an aliphatic carboxylate ion Examples are methyltriphenylphosphonium acetate, ethyltriphenylphosphonium acetate, and n-propyltriphenylphosphonium acetate.

(12) Phosphonium salt in which three of $R^1$, $R^2$, $R^3$ and $R^4$ are aryl groups, one is an alkyl group, and $X^-$ is a fluoroborate ion Examples are methyltriphenylphosphonium fluoroborate, ethyltriphenylphosphonium fluoroborate, and n-propyltriphenylphosphonium fluoroborate.

(13) Phosphonium salt in which two of $R^1$, $R^2$, $R^3$ and $R^4$ are aryl groups, other two are other groups, and $X^-$ is a halide ion Examples are dimethyldiphenylphosphonium chloride, diethyldiphenylphosphonium chloride, dimethyldiphenylphosphonium bromide, and diethyldiphenylphosphonium bromide.

(14) Phosphonium salt in which one of $R^1$, $R^2$, $R^3$ and $R^4$ aryl groups, other three are other groups, and $X^-$ is a halide ion Examples are diethylmethylphenylphosphonium chloride, and diethylmethylphenylphosphonium bromide.

(15) Phosphonium salt in which none of $R^1$, $R^2$, $R^3$ and $R^4$ are aryl groups, and $X^-$ is a halide ion Examples are tetra-n-butylphosphonium chloride, and tetra-n-butylphosphonium bromide.

Some of the above-mentioned phosphonium salts are known and available on market. Other phosphonium salts can be prepared by the processes set forth in Bull. Chem. Soc. Jpn., 56, 2869 (1983) and J. Am. Chem. Soc., 70, 737 (1948), or processes similar to those described in these publications.

For instance, the tetraarylphosphonium chloride can be prepared by reacting a triarylphosphine and an aryl halide (e.g., aryl iodide or aryl bromine) in the presence of a palladium acetate catalyst and treating the resulting tetraarylphosphonium iodide or bromide with an ion exchange resin (chloride type) to give the desired tetraarylphosphonium chloride. The produced tetraarylphosphonium chloride is preferably dried. For the drying, the tetraarylphosphonium chloride is preferably heated to 100° to 200° C. for 0.5 to 5 hours in a stream of a dry inert gas such as dry argon gas and then heated to 80° to 200° C. for 0.5 to 2 hours in a stream of a dry hydrogen chloride gas. The commercially available tetraarylphosphonium chloride is also preferred to be subjected to the above-mentioned process.

The tetraarylphosphonium salt having a counter ion other than halide ion can be prepared by reacting the above-obtained tetraarylphosphonium chloride with an alkali metal salt (e.g., sodium salt or potassium salt) or an ammonium salt of the desired counter ion, that is, ion exchange reaction. Other phosphonium salts other than the tetraaryl phosphonium salts can be prepared in the same manner or an analogous manner. These phosphonium salts are also preferred to be subjected to the drying treatment, in advance of its use as the catalyst.

(B) Phosphine

Formula (B):

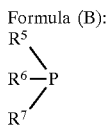

The phosphine can be represented by the above formula (B), wherein each of $R^5$, $R^6$ and $R^7$ independently represents an aryl group, an alkyl group of 1 to 16 carbon atoms, an aralkyl group of 7 to 22 carbon atoms, or a heterocyclic group of 4 to 16 carbon atoms. Any two of $R^5$, $R^6$ and $R^7$ may be combined to form a ring having the phosphorus atom as its ring member.

Examples of the aryl group, alkyl group, aralkyl group and heterocyclic group are the same as those described for the phosphonium salt of the formula (A).

The groups of $R^5$, $R^6$ and $R^7$ of the phosphine can be the same or different from each other. For instance, all of the groups of $R^5$, $R^6$ and $R^7$ are aryl groups in one phosphine, that is, a triarylphosphine. Two of the groups are aryl groups and other one is another group, that is, a diarylphosphine. Only one of the groups is an aryl group and other two are other groups, that is, an arylphosphine. All of the groups of $R^5$, $R^6$ and $R^7$ are other than the aryl groups. Preferred is the phosphine in which all of the groups of $R^5$, $R^6$ and $R^7$ are aryl groups.

Concrete examples of the preferred phosphines of the formula (B) are described below.

(1) Phosphine in which all of $R^5$, $R^6$ and $R^7$ are aryl groups (i.e., triarylphosphine)

Examples are triphenylphosphine, tris(p-chlorophenyl)phosphine, tris(p-tolyl)phosphine, and α-naphthyl(phenyl)-p-methoxyphenylphosphine.

(2) Phosphine in which two of $R^5$, $R^6$ and $R^7$ are aryl groups and one is other group (i.e., diarylphosphine)

Examples are methyldiphenylphosphine and phenyl-(p-methoxyphenyl)methylphosphine.

(3) Phosphine in which one of $R^5$, $R^6$ and $R^7$ is an aryl group and other two are other groups (i.e., arylphosphine)

Examples are dimethyl(phenyl)phosphine and ethyl(phenyl)-n-propylphosphine.

(4) Phosphine in which none of $R^5$, $R^6$ and $R^7$ are aryl groups

Examples are benzyl-(n-butyl)methylphosphine and tributylphosphine. An example of a phosphine in which any two of $R^5$, $R^6$ and $R^7$ are combined to form a ring having the phosphorus atom as its ring member is phenylbiphenylenephosphine.

(C) Phosphine Dihalide

Formula (C):

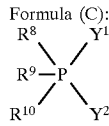

The phosphine dihalide can be represented by the above formula (C), wherein each of $R^8$, $R^9$ and $R^{10}$ independently represents an aryl group, an alkyl group of 1 to 16 carbon atoms, an aralkyl group of 7 to 22 carbon atoms, or a heterocyclic group of 4 to 16 carbon atoms, and each of $Y^1$ and $y^2$ independently represents a halogen atom such as chlorine, bromine or iodine. Any two of $R^8$, $R^9$ and $R^{10}$ may be combined to form a ring having the phosphorus atom as its ring member.

Examples of the aryl group, alkyl group, aralkyl group and heterocyclic group are the same as those described for the phosphonium salt of the formula (A).

The groups of $R^8$, $R^9$ and $R^{10}$ of the phosphine dihalide can be the same or different from each other. For instance, all of the groups of $R^8$, $R^9$ and $R^{10}$ are aryl groups in one phosphine, that is, a triarylphosphine dihalide. Two of the groups are aryl groups and other one is another group, that is, a diarylphosphine dihalide. Only one of the groups is an aryl group and other two are other groups, that is, an arylphosphine dihalide. All of the groups of $R^8$, $R^9$ and $R^{10}$ are other than the aryl groups. Preferred is the phosphine dihalide in which all of the groups of $R^8$, $R^9$ and $R^{10}$ are aryl groups.

Concrete examples of the preferred phosphine dihalides of the formula (C) are triphenylphosphine dichloride, triphenylphosphine dibromide, and triphenylphosphine diiodide.

(D) Phosphine Oxide

Formula (D):

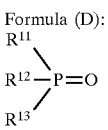

The phosphine oxide can be represented by the above formula (D), wherein each of $R^{11}$, $R^{12}$ and $R^{13}$ independently represents an aryl group, an alkyl group of 1 to 16 carbon atoms, an aralkyl group of 7 to 22 carbon atoms, or a heterocyclic group of 4 to 16 carbon atoms. Any two of $R^{11}$, $R^{12}$ and $R^{13}$ may be combined to form a ring having the phosphorus atom as its ring member.

Examples of the aryl group, alkyl group, aralkyl group and heterocyclic group are the same as those described for the phosphonium salt of the formula (A).

The groups of $R^{11}$, $R^{12}$ and $R^{13}$ of the phosphine oxide can be the same or different from each other. For instance, all of the groups of $R^{11}$, $R^{12}$ and $R^{13}$ are aryl groups in one phosphine, that is, a triarylphosphine oxide. Two of the groups are aryl groups and other one is another group, that is, a diarylphosphine oxide. Only one of the groups is an aryl group and other two are other groups, that is, an arylphosphine oxide. All of the groups the groups of $R^{11}$, $R^{12}$ and $R^{13}$ are other than the aryl groups. Preferred is the phosphine oxide in which all of the groups of $R^{11}$, $R^{12}$ and $R^{13}$ are aryl groups.

Concrete examples of the preferred phosphine oxides of the formula (D) are described below.

(1) Phosphine oxide in which all of $R^{11}$, $R^{12}$ and $R^{13}$ are aryl groups (i.e., triarylphosphine oxide)

Examples are triphenylphosphine oxide, tris(p-chlorophenyl)phosphine oxide, tris(p-tolyl)phosphine oxide, and α-naphthyl(phenyl)-p-methoxyphenylphosphine oxide.

(2) Phosphine oxide in which two of $R^{11}$, $R^{12}$ and $R^{13}$ are aryl groups and one is other group (i.e., diarylphosphine oxide)

Examples are methyldiphenylphosphine oxide and phenyl-(p-methoxyphenyl)methylphosphine oxide.

(3) Phosphine oxide in which one of $R^{11}$, $R^{12}$ and $R^{13}$ is an aryl group and other two are other groups (i.e., aryl phosphine oxide)

Examples are dimethyl(phenyl)phosphine oxide and ethyl(phenyl)n-propylphosphine oxide.

(4) Phosphine oxide in which none of $R^{11}$, $R^{12}$ and $R^{13}$ are aryl groups Examples are benzyl-(n-butyl)methylphosphine oxide and tributylphosphine oxide. An example of a phosphine in which any two of $R^{11}$, $R^{12}$ and $R^{13}$ are combined to form a ring having the phosphorus atom as its ring member is phenylbiphenylenephosphine oxide.

Among the above-mentioned organic phosphorus compounds, tetraarylphosphonium halide, tetraarylphosphonium hydrogen dihalide, and triarylphosphine dihalide are preferred. Most preferred are tetraarylphosphonium chloride, tetraarylphosphonium hydrogen dichloride, and triarylphosphine dichloride. The organic phosphorus compound can be employed singly or in combination in the process of the present invention. The organic phosphorus compound can be dissolved or dispersed in the reaction medium.

The organic phosphorus compound can be employed in an amount of 0.001 to 50 mol. %, preferably 0.01 to 20 mol. %, based on the amount of diaryl oxalate (100 mol. %).

In the reaction for releasing or eliminating carbon monoxide (CO) according to the invention, a halogen atom-containing compound can be incorporated. Particularly, in the cases where a phosphonium salt other than phosphonium halide and phosphonium hydrogen dihalide are used as the phosphorus compound and where a phosphonium halide or a phosphonium hydrogen dihalide is used in a small amount, the incorporation of a halogen atom-containing compound is preferred. The halogen atom-containing compound preferably is a chlorine atom-containing compound or a bromine atom-containing compound. Most preferred is a chlorine atom-containing compound. The incorporated halogen atom-containing compound can be decomposed or converted into other halogen atom-containing compound in the course of the development of the reaction.

The halogen atom-containing compound is generally employed in an amount of 0.001 to 300 moles, preferably 0.1 to 100 moles per one mole of the organic phosphorus compound.

The halogen atom-containing compound may be an inorganic compound or an organic compound.

Examples of the inorganic halogen atom-containing compounds are halides of aluminum (e.g., aluminum chloride and aluminum bromide), halides of metals belonging to the platinum group (e.g., platinum chloride, ruthenium chloride, palladium chloride, and chloroplatinic acid), halides of phosphorus (e.g., phosphorus trichloride, phosphorus pentachloride, phosphorus oxychloride, phosphorus tribromide, phosphorus pentabromide, and phosphorus oxybromide), hydrogen halides (e.g., hydrogen chloride and hydrogen bromide), halides of sulfur (e.g., thionyl chloride, sulfuryl chloride, sulfur dichloride, and disulfur dichloride), and halogens per se (e.g., chlorine and bromine).

The organic halogen atom-containing compound preferably contains (1) carbon atom, (2) a halogen atom such as chlorine atom or a bromine atom, and (3) at least one of other atoms selected from a hydrogen atom, a nitrogen atom, a sulfur atom, and a silicon atom.

Examples of the organic halogen atom-containing compounds are organic compounds having a C—Hal bonding (in which Hal means a halogen atom), a C—Si—Hal bonding, a C(O)—Hal bonding or a C—S(O)$_2$—Hal bonding. The organic halogen atom-containing compound can contain one or more halogen atoms such as chlorine(s), bromine(s) or iodine(s) singly or in combination.

Examples of the organic compound having a C—Hal bonding include alkyl halides (e.g., chloroform, carbon tetrachloride, 1,2-dichloroethane, butyl chloride, and dodecyl chloride), aralkyl halides (e.g., benzyl chloride, benzotrichloride, triphenylmethyl chloride, and α-bromo-o-xylene), and halogenated aliphatic nitriles (e.g., β-chloropropionitrile, and γ-chlorobutyronitrile), halogenated aliphatic carboxylic acids (e.g., chloroacetic acid, bromoacetic acid, and chloropropionic acid).

Examples of the organic compound having a C—Si—Hal bonding include halogenated silanes (e.g., diphenyldichlorosilane, and triphenylchlorosilane).

Examples of the organic compound having a C(O)—Hal bonding include acyl halides (e.g., acetyl chloride, oxalyl chloride, propionyl chloride, stearoyl chloride, benzoyl chloride, 2-naphthalenecarboxylic acid chloride, and 2-thiophenecarboxylic acid chloride), halogenated formic acid aryl esters (e.g., phenyl chloroformate), and halogenated glyoxylic acid aryl esters (e.g., phenyl chloroglyoxylate).

Examples of the organic compound having a C—S(O)$_2$—Hal bonding include sulfonyl chlorides (e.g., p-toluenesulfonic acid chloride, and 2-naphthalenesulfonic acid chloride).

The reaction for releasing CO from the diaryl oxalate according to the invention can be conducted at a temperature in the range of 100° to 450° C., preferably 160° to 450° C., more preferably 180° to 400° C., most preferably 180° to 350° C., in an appropriate reaction vessel in the presence of the organic phosphorus compound, and optionally in combination with the halogen atom-containing compound. The reaction can be performed in a liquid phase in a batch system or a continuous system. In the course of progress of the reaction, carbon monoxide is emitted and the desired diaryl carbonate is formed. The reaction can be conducted under an atmospheric pressure, under a certain pressure, or under a reduced pressure. If the reaction temperature is higher than the reflux temperature of the starting diaryl oxalate, the reaction is preferably performed under pressure. There are no specific limitations with respect to the material of the reaction vessel. Ordinary reaction vessels such as vessels of glass or stainless (SUS) can be employed.

The reaction does not require any solvent. However, if necessary, an organic solvent which does not pertain in the reaction can be employed. Such solvents can be diphenyl ether, sulforane, N-methylpyrrolidone, dimethylimidazolidone, or 1,3-dimethyl-3,4,5,6-tetrahydro-2(1H)-pyrimidinone.

After the reaction is complete, the resulting diaryl carbonate can be recovered and isolated by distillation.

Other decarbonylation reactions for which the catalyst of the invention is employable are now described.

Decarbonylation of an aryl haloglyoxylate to prepare an aryl haloformate can be done almost in the same manner as that described for the decarbonylation reaction of a diaryl oxalate to prepare a diaryl carbonate.

Examples of the aryl haloglyoxylate include phenyl chloroglyoxylate, 4-methylphenyl chloroglyoxylate, 4-methoxyphenyl chloroglyoxylate, and 4-chlorophenyl chloroglyoxylate. These aryl haloglyoxylates can be prepared by the method analogous to the methods described in Biochemistry, 19, 5505 (1980) and J. Am. Chem. Soc., 71, 2532 (1940).

The reaction for releasing CO from the aryl haloglyoxylate according to the invention can be conducted at a temperature in the range of 50° to 450° C., preferably 80° to 400° C., more preferably 100° to 350° C., in an appropriate reaction vessel in the presence of the organic phosphorus compound, and optionally in combination with the halogen atom-containing compound. The amounts of the organic phosphorus compound and the halogen atom-containing compound are essentially the same as those described above for the decarbonylation of the diaryl oxalate. The reaction can be performed in a liquid phase in a batch system or a continuous system. In the course of progress of the reaction, carbon monoxide is emitted and the desired aryl haloformate is formed. The reaction can be conducted under an atmospheric pressure, under a certain pressure, or under a reduced pressure. The reaction does not require any solvent. However, if necessary, an organic solvent which does not pertain in the reaction can be employed.

After the reaction is complete, the resulting aryl haloformate can be recovered and isolated by distillation.

Decarbonylation of an aryl or alkyl arylglyoxylate to prepare an aromatic carboxylic acid aryl or alkyl ester, respectively, can be done almost in the same manner as that described for the decarbonylation reaction of a diaryl oxalate to prepare a diaryl carbonate.

Examples of the aryl arylglyoxylate include phenyl phenylglyoxylate and 4-chlorophenyl phenylglyoxylate.

Examples of the alkyl arylglyoxylate include methyl phenylglyoxylate and ethyl phenylglyoxylate.

The reaction for releasing CO from the aryl arylglyoxylate according to the invention can be conducted at a temperature in the range of 100° to 450° C., preferably 160° to 400° C., more preferably 180° to 350° C., in an appropriate reaction vessel in the presence of the organic phosphorus compound, and optionally in combination with the halogen atom-containing compound. The amounts of the organic phosphorus compound and the halogen atom-containing compound are essentially the same as those described above for the decarbonylation of the diaryl oxalate.

The reaction can be performed in a liquid phase in a batch system or a continuous system. In the course of progress of the reaction, carbon monoxide is emitted and the desired product is formed. The reaction can be conducted under an atmospheric pressure, under a certain pressure, or under a reduced pressure. The reaction does not require any solvent. However, if necessary, an organic solvent which does not pertain in the reaction can be employed.

After the reaction is complete, the resulting product can be recovered and isolated by distillation.

Decarbonylation of a heterocyclic glyoxylic acid aryl ester to prepare a heterocyclic carbolylic acid aryl ester can be done almost in the same manner as that described for the decarbonylation reaction of a diaryl oxalate to prepare a diaryl carbonate.

Examples of the heterocyclic acid aryl ester include phenyl 2-thienylglyoxylate and phenyl 2-furylglyoxylate.

The reaction for releasing CO from the heterocyclic acid aryl ester according to the invention can be conducted at a temperature in the range of 50° to 450° C., preferably 80° to 400° C., more preferably 100° to 350° C., in an appropriate reaction vessel in the presence of the organic phosphorus compound, and optionally in combination with the halogen atom-containing compound. The amounts of the organic phosphorus compound and the halogen atom-containing compound are essentially the same as those described above for the decarbonylation of the diaryl oxalate.

The reaction can be performed in a liquid phase in a batch system or a continuous system. In the course of progress of the reaction, carbon monoxide is emitted and the desired heterocyclic carboxylic acid aryl ester is formed. The reaction can be conducted under an atmospheric pressure, under a certain pressure, or under a reduced pressure. The reaction does not require any solvent. However, if necessary, an organic solvent which does not pertain in the reaction can be employed.

After the reaction is complete, the resulting product can be recovered and isolated by distillation.

Decarbonylation of a dialkyl oxalate to prepare a dialkyl carbonate can be done almost in the same manner as that described for the decarbonylation reaction of a diaryl oxalate to prepare a diaryl carbonate.

Examples of the dialkyl oxalates include dimethyl oxalate, diethyl oxalate, and methyl ethyl oxalate.

The reaction for releasing CO from the dialkyl oxalate according to the invention can be conducted at a temperature in the range of 100° to 450° C., preferably 140° to 350° C., more preferably 160° to 300° C., in an appropriate reaction vessel in the presence of the organic phosphorus compound, and optionally in combination with the halogen atom-containing compound. The amounts of the organic phosphorus compound and the halogen atom-containing compound are essentially the same as those described above for the decarbonylation of the diaryl oxalate.

The reaction can be performed in a liquid phase in a batch system or a continuous system. In the course of progress of the reaction, carbon monoxide is emitted and the desired dialkyl carbonate is formed. The reaction is generally conducted under pressure. The reaction does not require any solvent. However, if necessary, an organic solvent which does not pertain in the reaction can be employed.

After the reaction is complete, the resulting dialkyl carbonate can be recovered and isolated by distillation.

The present invention is further described by the following non-limitative examples. In the examples, the "conversion ratio of diaryl oxalate" (i.e., ratio of amount of consumed (or reacted) diaryl oxalate per the amount of charged diaryl oxalate), "selectivity to diaryl carbonate" (i.e., ratio of the amount of produced diaryl carbonate per the amount of consumed diaryl oxalate), "Yield" (i.e., ratio of the amount of produced diaryl carbonate per the amount of charged diaryl oxalate) for decarbonylation reaction of the diaryl oxalate, and the like are all expressed in terms of molar percent ratio (i.e., mol.6). For the decarbonylation reactions of other compounds, essentially the same expressions are given.

Reference Example 1

Synthesis of p-chlorophenyltriphenylphosphonium iodide [Reference: Bull. Chem. Soc. Jpn., 56, 2869 (1983)]

In 100 mL-volume egg-plant type flask, 3.30 g (11.4 mmol.) of triphenylphosphine and 3.00 g (12.6 mmol.) of p-chloroiodobenzene were dissolved in 40 mL of xylene. To the solution was added 30.0 mg (0.134 mmol.) of palladium acetate, and the resulting mixture was stirred at 150° C. for 9.5 hours. After the reaction was complete, the reaction mixture was cooled to room temperature, and the precipitate was collected on a filter by suction. The collected precipitate was washed with xylene and dried under reduced pressure at 130° C. for 3 hours. There was obtained 5.48 g (yield: 87%) of p-chlorophenyltriphenylphosphonium iodide (m.p.: 219°–222° C., elemental analysis: found: C 57.84%, H 3.74%, calculated: C 57.57%, H 3.82%).

Reference Example 2

Synthesis of p-chlorophenyltriphenylphosphonium chloride [Reference: J. Am. Chem. Soc., 70, 737 (1948)]

In 50 mL-volume egg-plant type flask, 1.00 g (2.00 mmol.) of p-chlorophenyltriphenylphosphonium iodide and 10 mL (14 mg equivalent) of Amberlite IRA-400 (highly basic ion exchange resin, chloro-type, available from Organo Co., Ltd.) were stirred in an ion-exchanged water at room temperature for 1 hour. Subsequently, the ion exchange resin was filtered off, and the resin was washed with a small amount of an ion-exchanged water. The washing and the filtrate were combined to obtain 25 mL of an aqueous solution. To the solution was added 6.50 g of sodium chloride. The precipitate produced was collected on a filter by suction and dissolved in 30 mL of methylene chloride. Insolubles were filtered off, and the filtrate was added to 30 mL of ether. The precipitate produced was washed with ether and successively dried in the stream of dry argon gas at 120° C. for 1 hour, at 150° C. for 1 hour, and 180° C. for 1 hour. The dried product was then placed in contact with a stream of dry hydrogen chloride at 180° C. for 30 minutes. Thus treated product was further heated to 180° C. in a stream of dry argon gas for 1 hour, and then cooled to room temperature. There was obtained 0.63 g (yield: 77%) of p-chlorophenyltriphenylphosphonium chloride (m.p.: 158°–160° C.).

Reference Example 3

Synthesis of tetraphenylphosphonium thiocyanide

In 50 mL-volume egg-plant type flask, 1 g of tetraphenylphosphonium chloride was dissolved in 10 mL of water.

To the solution was added 10 mL of an aqueous solution containing a theoretical amount of ammonium thiocyanate. The resulting mixture was stirred at room temperature for 0.5 hour. The precipitate produced was collected by filtration and washed with water three times. The precipitate was then re-precipitated from a mixture of methylene chloride and ether (½, vol/vol). The precipitate was washed with methylene chloride and dried at 160°–200° C. in a stream of argon under reduced pressure. There was obtained 0.88 g (yield: 83w) of tetraphenylphosphonium thiocyanide (m.p.: over 300° C.).

Other Reference Examples

Various phosphonium chlorides were prepared from the corresponding iodides or bromides in the similar manner as those described in Reference Examples 1 and 2. The products were heated and treated with hydrogen chloride in the similar manner as those in Reference Example 2 before they were employed as catalyst. Tetraphenylphosphonium trifluoroacetate was prepared in the similar manner as that in Reference Example 3.

The yields and other data of the produced phosphonium salts are set forth in Table 1.

TABLE 1

| Phosphonium Salt | X | Yield (%) | M.P. (°C.) | Analysis (Found) C | H | N |
|---|---|---|---|---|---|---|
| (p-F-Ph)$_4$P.X | I | 75 | >300 | 53.33 | 2.85 | — |
| | Cl | 97 | >300 | | | |
| (p-Cl-Ph)$_4$P.X | I | 56 | >300 | 47.79 | 2.47 | — |
| | Cl | 96 | >300 | | | |
| (p-Me-Ph)$_4$P.X | I | 58 | 275–278 | 64.20 | 5.11 | — |
| | Cl | 93 | >300 | | | |
| (p-Cl-Ph)PPh$_3$.X | I | 87 | 219–222 | 57.84 | 3.74 | — |
| | Cl | 77 | 158–160 | | | |
| (p-Me-Ph)PPh$_3$.X | I | 85 | 214–217 | 62.43 | 4.61 | — |
| | Cl | 98 | 177–180 | | | |
| (p-Ph-Ph)PPh$_3$.X | Br | 42 | 210–214 | 72.62 | 4.86 | — |
| | Cl | 86 | 225–229 | | | |
| (p-MeO-Ph)PPh$_3$.X | I | 87 | 223–226 | 60.20 | 4.37 | — |
| | Cl | 78 | 215–218 | | | |
| (p-Me$_2$N-Ph)PPh$_3$.X | Br | 84 | 278–282 | 67.52 | 5.57 | 3.04 |
| | Cl | 76 | 270–273 | | | |
| (p-EtO$_2$C-Ph)PPh$_3$.X | I | 59 | 215–218 | 60.41 | 4.44 | — |
| | Cl | 69 | 91–95 | | | |
| (m-CF$_3$-Ph)PPh$_3$.X | I | 32 | 194–197 | 56.50 | 3.53 | — |
| | Cl | 68 | 145–149 | | | |
| (m-MeO-Ph)PPh$_3$.X | I | 84 | 204–207 | 60.51 | 4.47 | — |
| | Cl | 79 | 260–267 | | | |
| (m-NC-Ph)PPh$_3$X | Br | 9 | 222–225 | 67.82 | 4.38 | 2.91 |
| | Cl | 99 | 100–105 | | | |
| (i-naphthyl)PPh$_3$.X | I | 25 | 282–285 | 65.14 | 4.13 | — |
| | Cl | 84 | 271–274 | | | |
| (2-thiophene)PPh$_3$.X | I | 32 | 288–290 | 56.22 | 3.79 | — |
| | Cl | 99 | 162–165 | | | |
| Ph$_4$P.X | SCN | 83 | >300 | 75.46 | 5.06 | 3.67 |
| Ph$_4$P.X | CF$_3$CO$_2$ | 69 | 227 | 69.00 | 4.39 | — |

EXAMPLE 1

In a 50 mL-volume glass flask equipped with a thermometer, a stirrer and a reflux condenser, a mixture of 6.0 g (24.8 mmol.) of diphenyl oxalate and 0.093 g (0.25 mmol.) of tetraphenylphosphonium chloride (PPh$_4$.Cl) was heated to 255° C. under an atmospheric pressure. At that temperature, the mixture was subjected to decarbonylation reaction (reaction for releasing CO) for 3 hours with removal of the produced carbon monoxide. The tetraphenylphosphonium chloride was heated and treated with hydrogen chloride in the same manner as those described in Reference Example 2, before it was employed as the catalyst.

After the reaction was complete, the reaction mixture was cooled to room temperature and analyzed by gas chromatography. It was confirmed that the conversion ratio of diphenyl oxalate was 96.2%, and 5.05 g (23.6 mmol.) of diphenyl carbonate was produced; selectivity 99.0%; yield 95.2%.

EXAMPLES 2 TO 4

The decarbonylation reaction was repeated in the manner as described in Example 1, except that the amount of tetraphenylphosphonium chloride, the amount of diphenyl oxalate, the reaction temperature and the reaction time were changed as set forth in Table 2.

The results are also set forth in Table 2.

EXAMPLES 5 TO 9

The decarbonylation reaction was repeated in the manner as described in Example 1, except that tetraphenylphosphonium chloride was replaced with that set forth in Table 2, and that the amount of diphenyl oxalate, the reaction temperature and the reaction time were changed as set forth in Table 2. The tetraphenylphosphonium bromide employed was of the commercially available grade. The tetraphenylphosphonium hydrogen dichloride was prepared the known process (Z. anorg. allg. chem., 551, 179 (1987).

The results are also set forth in Table 2.

TABLE 2

| Example No. | Catalyst (mol. % to DPO) | DPO (mmol) | Tem. (°C.) | Time (hr.) | DPO Con. (%) | DPC Sel. (%) | DPC Yield (%) |
|---|---|---|---|---|---|---|---|
| Ex.1 | Ph$_4$P.Cl (1) | 24.8 | 255 | 3 | 96.2 | 99.0 | 95.2 |
| Ex.2 | Ph$_4$P.Cl (5) | 20.7 | 220 | 3 | 99.0 | 99.0 | 98.0 |
| Ex.3 | Ph$_4$P.Cl (10) | 20.7 | 200 | 3 | 97.8 | 96.6 | 94.5 |
| Ex.4 | Ph$_4$P.Cl (0.2) | 20.7 | 280 | 1 | 98.0 | 99.0 | 97.0 |
| Ex.5 | Ph$_4$P.Br (4.3) | 19.6 | 260 | 1 | 69.0 | 82.0 | 56.6 |
| Ex.6 | Ph$_4$Ph$_4$HCl$_2$ (0.5) | 20.7 | 260 | 3 | 99.0 | 99.0 | 98.0 |
| Ex.7 | (p-F-Ph)$_4$P.Cl(0.5) | 20.7 | 260 | 3 | 99.0 | 99.0 | 98.0 |
| Ex.8 | (p-Cl-Ph)$_4$P.Cl(0.5) | 20.7 | 260 | 3 | 99.0 | 99.0 | 98.0 |
| Ex.9 | (p-Me-Ph)$_4$P.Cl(0.5) | 20.7 | 260 | 3 | 65.0 | 90.0 | 58.5 |

Remarks:

The amount of the catalyst (organic phosphorus compound) is set forth in terms of mol. % based on the amount of DPO (diphenyl oxalate).

DPC: diphenyl carbonate

Ph$_4$P.Cl: tetraphenylphosphonium chloride

Ph$_4$P.Br: tetraphenylphosphonium bromide

Ph$_4$P.HCl$_2$: tetraphenylphosphonium hydrogen dichloride (p-F—Ph)$_4$P.Cl: tetrakis(p-fluorophenyl)phosphonium chloride (p-Cl—Ph)$_4$P.Cl: tetrakis(p-chlorophenyl)phosphonium chloride (p-Me—Ph)$_4$P.Cl: tetrakis(p-tolyl)phosphonium chloride Comparison Example 1

The decarbonylation reaction was repeated in the manner as described in Example 1, except that 3.97 g (16.4 mmol) of diphenyl oxalate was employed and no tetraphenylphosphonium chloride was employed.

It was confirmed that the conversion ratio of diphenyl oxalate (DPO) was 0%, and that no diphenyl carbonate (DPC) was produced.

Comparison Example 2

The decarbonylation reaction was repeated in the manner as described in Example 1, except that 5.0 g (20.7 mmol) of diphenyl oxalate was employed, the reaction temperature was changed to 330° C., and no tetraphenylphosphonium chloride was employed.

It was confirmed that the conversion ratio of diphenyl oxalate was 10.8%, and that 0.18 g (0.84 mmol) of diphenyl carbonate was produced; selectivity 37.7%; yield 4.1%.

Comparison Example 3

In a closable 90 mL-volume stainless-made reaction vessel equipped with a thermometer and a stirrer, a mixture of 5.0 g (20.7 mmol) of diphenyl oxalate, 0.5 g (3.8 mmol) of potassium phenolate, and 5.0 g of tetrahydrofuran was heated to 100° C. At that temperature, the mixture was subjected to decarbonylation reaction for 3 hours.

It was confirmed that the conversion ratio of diphenyl oxalate was 0%, and that no diphenyl carbonate was produced.

The reaction conditions and results of Comparison Examples 1 to 3 are set forth in Table 3.

TABLE 3

| Com. Ex. No. | Catalyst (mol. % to DPO) | DPO (mmol) | Tem. (°C.) | Time (hr.) | DPO Con. (%) | DPC Sel. (%) | DPC Yield (%) |
|---|---|---|---|---|---|---|---|
| Com.Ex.1 | — | 16.4 | 255 | 3 | 0 | 0 | 0 |
| Com.Ex.2 | — | 20.7 | 330 | 3 | 10.8 | 37.7 | 4.1 |
| Com.Ex.3 | PhOK (18) | 20.7 | 100 | 3 | 0 | 0 | 0 |

Remarks:

The amount of the catalyst(potassium phenolate) is set forth in terms of mol. % based on the amount of DPO (diphenyl oxalate).

PhOK: potassium phenolate

EXAMPLES 10 TO 18

The decarbonylation reaction was repeated in the manner as described in Example 1, except that tetraphenylphosphonium chloride was replaced with the phosphonium salt set forth in Table 4, and that the amount of diphenyl oxalate and the reaction temperature were changed as set forth in Table 4.

The results are also set forth in Table 4.

TABLE 4

| Example No. | Catalyst (0.5 mol. % to DPO) | DPO (mmol) | Tem. (°C.) | Time (hr.) | DPO Con. (%) | DPC Sel. (%) | DPC Yield (%) |
|---|---|---|---|---|---|---|---|
| Ex.10 | (p-Cl-Ph)PPh$_3$.Cl | 20.7 | 260 | 3 | 99.0 | 98.0 | 97.0 |
| Ex.11 | (p-Me-Ph)PPh$_3$.Cl | 20.7 | 260 | 3 | 97.0 | 98.0 | 95.1 |
| Ex.12 | (p-Ph-Ph)PPh$_3$.Cl | 20.7 | 260 | 3 | 99.0 | 98.0 | 97.0 |
| Ex.13 | (p-MeO-Ph)PPh$_3$.Cl | 20.7 | 260 | 3 | 67.0 | 61.0 | 40.9 |
| Ex.14 | (p-Me$_2$N-Ph)PPh$_3$.Cl | 20.7 | 260 | 3 | 99.0 | 99.0 | 98.0 |
| Ex.15 | (p-EtO$_2$C-Ph)PPh$_3$.Cl | 20.7 | 260 | 3 | 85.0 | 99.0 | 84.2 |
| Ex.16 | (m-CF$_3$-Ph)PPh$_3$.Cl | 20.7 | 260 | 3 | 96.0 | 99.0 | 95.0 |
| Ex.17 | (m-MeO-Ph)PPh$_3$.Cl | 20.7 | 260 | 3 | 97.0 | 97.0 | 94.1 |
| Ex.18 | (m-NC-Ph)PPh$_3$.Cl | 20.7 | 260 | 3 | 96.0 | 98.0 | 94.1 |

Remarks:

(p-Cl—Ph)PPh$_3$.Cl: p-chlorophenyltriphenylphosphonium chloride (p-Me—Ph)PPh$_3$.Cl: p-tolyltriphenylphosphonium chloride (p-Ph—Ph)PPh$_3$.Cl: p-biphenyltriphenylphosphonium chloride (p-MeO—Ph)PPh$_3$.Cl: p-methoxyphenyltriphenylphosphonium chloride (p-Me$_2$N—Ph)PPh$_3$.Cl: p-dimethylaminophenyltriphenylphosphonium chloride (p-EtO$_2$C—Ph)PPh$_3$.Cl: p-ethoxycarbonylphenyltriphenylphosphonium chloride (m-CF$_3$—Ph)PPh$_3$.Cl: m-trifluoromethylphenyltriphenylphosphonium chloride (m-MeO—Ph)PPh$_3$.Cl: m-methoxyphenyltriphenylphosphonium chloride (m-NC—Ph)PPh$_3$.Cl: m-cyanophenyltriphenylphosphonium chloride

EXAMPLES 19 TO 23

The decarbonylation reaction was repeated in the manner as described in Example 1, except that tetraphenylphosphonium chloride was replaced with the phosphonium salt set forth in Table 5, and that the amount of diphenyl oxalate and the reaction temperature were changed as set forth in Table 5.

The results are also set forth in Table 5.

TABLE 5

| Example No. | Catalyst (mol. % to DPO) | DPO (mmol) | Tem. (°C.) | Time (hr.) | DPO Con. (%) | DPC Sel. (%) | DPC Yield (%) |
|---|---|---|---|---|---|---|---|
| Ex.19 | (1-na)PPh$_3$.Cl(0.5) | 20.7 | 260 | 3 | 99.0 | 99.0 | 98.0 |
| Ex.20 | (2-th)PPh$_3$.Cl(0.5) | 20.7 | 260 | 3 | 99.0 | 99.0 | 98.0 |
| Ex.21 | MePPh$_3$.Br(5) | 20.7 | 255 | 3 | 45.1 | 64.5 | 29.1 |
| Ex.22 | ClCH$_2$-PPh$_3$.Cl(0.5) | 20.7 | 260 | 3 | 35.0 | 96.0 | 33.6 |
| Ex.23 | PhCH$_2$-PPh$_3$.Cl(0.5) | 20.7 | 260 | 3 | 47.0 | 89.0 | 41.8 |
| Ex.24 | (p-Cl-Ph)$_3$P(5) | 24.8 | 255 | 3 | 99.4 | 81.6 | 81.1 |
| Ex.25 | Ph$_3$PCl$_2$(5) | 24.8 | 255 | 3 | 98.7 | 93.0 | 91.8 |
| Ex.26 | Ph$_3$P=O(5) | 24.8 | 255 | 3 | 11.6 | 94.0 | 10.9 |

Remarks:

(1-na)PPh$_3$.Cl: 1-naphthyltriphenylphosphonium chloride (2-th)PPh$_3$.Cl: 2-thiophenetriphenylphosphonium chloride MePPh$_3$.Br: methyltriphenylphosphonium bromide ClCH$_2$—PPh$_3$.Cl: chloromethyltriphenylphosphonium chloride PhCH$_2$—PPh$_3$.Cl: benzyltriphenylphosphonium chloride (p-Cl—Ph)$_3$P: tris(p-chlorophenyl)phosphine Ph$_3$PCl$_2$: triphenylphosphine dichloride
Ph$_3$P=O: triphenylphosphine oxide

EXAMPLE 24

The decarbonylation reaction was repeated in the manner as described in Example 1, except that tetraphenylphosphonium chloride was replaced with 1.24 mmol of tris(p-chlorophenyl)phosphine.

It was confirmed that the conversion ratio of diphenyl oxalate was 99.4%, the selectivity was 81.6%, and the yield was 81.1%.

EXAMPLE 25

The decarbonylation reaction was repeated in the manner as described in Example 1, except that tetraphenylphosphonium chloride was replaced with 1.24 mmol of triphenylphosphine dichloride.

It was confirmed that the conversion ratio of diphenyl oxalate was 98.7%, the selectivity was 93.0%, and the yield was 91.8%.

EXAMPLE 26

The decarbonylation reaction was repeated in the manner as described in Example 1, except that tetraphenylphosphonium chloride was replaced with 1.24 mmol of triphenylphosphine oxide. The charged diphenyl oxalate contained 3,000 ppm of chloride ion.

It was confirmed that the conversion ratio of diphenyl oxalate was 11.6%, the selectivity was 94.0%, and the yield was 10.9%.

EXAMPLE 27

The decarbonylation reaction was repeated in the manner as described in Example 1, except that tetraphenylphosphonium chloride was replaced with 1.24 mmol of triphenylphosphine, 0.25 mmol of aluminum trichloride was added, and the reaction temperature was changed as set forth in Table 6.

It was confirmed that the conversion ratio of diphenyl oxalate was 91.7%, the selectivity was 93.0%, and the yield was 85.3%.

EXAMPLES 28 TO 32

The decarbonylation reaction was repeated in the manner as described in Example 27, except that aluminum trichloride was replaced with the inorganic halogen atom-containing compound as set forth in Table 6, and the amount of diphenyl oxalate charged and the reaction temperature were changed as set forth in Table 6.

The reaction conditions and results are set forth in Table 6.

TABLE 6

| Example No. | Catalyst (5 mol. % to DPO) | Hal-Comp. (ratio) | DPO (mmol) | Tem. (°C.) | Time (hr.) | DPO Con. (%) | DPC Sel. (%) | DPC Yield (%) |
| --- | --- | --- | --- | --- | --- | --- | --- | --- |
| Ex.27 | Ph$_3$P | AlCl$_3$(0.2) | 24.8 | 270 | 3 | 91.7 | 93.0 | 85.3 |
| Ex.28 | Ph$_3$P | PtCl$_2$(1) | 24.8 | 245 | 3 | 30.6 | 89.5 | 27.4 |
| Ex.29 | Ph$_3$P | H$_2$PtCl$_6$(1) | 24.8 | 245 | 3 | 52.6 | 93.1 | 49.0 |
| Ex.30 | Ph$_3$P | RuCl$_3$(0.8) | 24.8 | 245 | 3 | 27.8 | 80.1 | 22.3 |
| Ex.31 | Ph$_3$P | SOCl$_2$(1) | 20.7 | 255 | 3 | 96.6 | 88.1 | 85.1 |
| Ex.32 | Ph$_3$P | Br$_2$(1) | 20.7 | 255 | 3 | 97.2 | 95.6 | 92.9 |

Remarks:

The amount of Hal-Comp. (i.e., halogen atom-containing compound) is indicated in terms of a molar ratio per one mole of the catalyst (i.e., organic phosphorus compound).

EXAMPLES 33 TO 46

The decarbonylation reaction was repeated in the manner as described in Example 27, except that aluminum trichloride was replaced with the organic halogen atom-containing compound as set forth in Table 7, and the amount of diphenyl oxalate charged and the reaction temperature were changed as set forth in Table 7.

The reaction conditions and results are set forth in Table 7.

TABLE 7

| Example No. | Catalyst (5 mol. % to DPO) | Hal-Comp. | DPO (mmol) | Tem. (°C.) | Time (hr.) | DPO Con. (%) | DPC Sel. (%) | DPC Yield (%) |
| --- | --- | --- | --- | --- | --- | --- | --- | --- |
| Ex.33 | Ph$_3$P | CHCl$_3$ | 20.7 | 255 | 3 | 32.4 | 86.1 | 27.9 |
| Ex.34 | Ph$_3$P | CCl$_4$ | 20.7 | 255 | 3 | 98.5 | 95.8 | 94.4 |
| Ex.35 | Ph$_3$P | C$_6$H$_5$CH$_2$Cl | 20.7 | 255 | 3 | 97.3 | 84.5 | 82.2 |
| Ex.36 | Ph$_3$P | (C$_6$H$_5$)$_3$CCl | 20.7 | 255 | 3 | 98.5 | 98.2 | 96.7 |
| Ex.37 | Ph$_3$P | (C$_6$H$_5$)$_2$SiCl$_2$ | 20.7 | 255 | 3 | 98.5 | 84.6 | 83.3 |
| Ex.38 | Ph$_3$P | ClCH$_2$CH$_2$CN | 20.7 | 255 | 3 | 91.3 | 83.6 | 76.3 |

TABLE 7-continued

| Example No. | Catalyst (5 mol. % to DPO) | Hal-Comp. | DPO (mmol) | Tem. (°C.) | Time (hr.) | DPO Con. (%) | DPC Sel. (%) | DPC Yield (%) |
|---|---|---|---|---|---|---|---|---|
| Ex.39 | Ph$_3$P | ClCH$_2$COOH | 20.7 | 255 | 3 | 92.1 | 87.2 | 80.3 |
| Ex.40 | Ph$_3$P | (COCl)$_2$ | 20.7 | 255 | 3 | 89.1 | 93.1 | 83.0 |
| Ex.41 | Ph$_3$P* | CH$_3$(CH$_2$)$_{16}$COCl | 20.7 | 255 | 3 | 29.0 | 96.0 | 27.8 |
| Ex.42 | Ph$_3$P | C$_6$H$_5$COCl | 20.7 | 255 | 3 | 92.8 | 85.8 | 79.6 |
| Ex.43 | Ph$_3$P* | C$_{10}$H$_7$COCl | 20.7 | 260 | 3 | 47.0 | 98.0 | 46.1 |
| Ex.44 | Ph$_3$P* | 2-thio-Cl | 20.7 | 260 | 3 | 35.0 | 99.0 | 34.7 |
| Ex.45 | Ph$_3$P | p-tolu-Cl | 20.7 | 255 | 3 | 95.9 | 80.9 | 77.6 |
| Ex.46 | Ph$_4$P | C$_{10}$H$_7$SO$_2$Cl | 20.7 | 255 | 3 | 74.6 | 79.0 | 58.9 |

Remarks:

*: 0.5 mol. %

The amount of Hal-Comp. (i.e., halogen atom-containing compound) employed is one mole to one mole of the catalyst, except the Examples 41 and 43 (3 moles per one mole of the catalyst) and Example 44 (2 moles per one mole of the catalyst).

(C$_6$H$_5$)$_2$SiCl$_2$: diphenyldichlorosilane

C$_{10}$H$_7$COCl: 2-naphthalenecarboxylic acid chloride

C$_{10}$H$_7$SO$_2$Cl: 2-naphthalenesulfonic acid chloride 2-thio-Cl: 2-thiophenecarboxylic acid chloride p-tolu-Cl: p-toluenesulfonic acid chloride

EXAMPLE 47

The decarbonylation reaction was repeated in the manner as described in Example 1, except that tetraphenylphosphonium chloride was replaced with 1.24 mmol of triphenylphosphine oxide, 0.50 mmol of aluminum trichloride was added, and the reaction temperature was changed as set forth in Table 8.

It was confirmed that the conversion ratio of diphenyl oxalate was 53.5%, the selectivity was 94.0%, and the yield was 50.3%.

EXAMPLES 48 TO 55

The decarbonylation reaction was repeated in the manner as described in Example 47, except that aluminum trichloride was replaced with the halogen atom-containing compound as set forth in Table 8, and the amount of diphenyl oxalate charged and the reaction temperature were changed as set forth in Table 8.

The reaction conditions and results are set forth in Table 8.

Remarks:

*: 20 mol. %

The amount of Hal-Comp. (i.e., halogen atom-containing compound) employed is one mole to one mole of the catalyst, except the Example 47 (0.4 mole per one mole of the catalyst).

Br-xylene: α-bromo-o-xylene p-tolu-Cl: p-toluenesulfonic acid chloride

EXAMPLE 56

The decarbonylation reaction was repeated in the manner as described in Example 1, except that the amount of tetraphenylphosphonium chloride was changed to 0.02 mmol, and the amount of diphenyl oxalate, the reaction temperature and the reaction time were changed as set forth in Table 9.

It was confirmed that the conversion ratio of diphenyl oxalate was 84.4%, the selectivity was 99.0%, and the yield was 83.6%.

EXAMPLES 57 TO 59

The decarbonylation reaction was repeated in the manner as described in Example 56, except that a halogen atom-containing compound was added as set forth in Table 9.

The reaction conditions and results are set forth in Table 9.

EXAMPLES 60 TO 67

The decarbonylation reaction was repeated in the manner as described in Example 1, except that tetraphenylphosphonium chloride was replaced with the tetraphenylphosphonium salt as set forth in Table 9, and the amount of diphenyl oxalate, the reaction temperature and the reaction time were changed as set forth in Table 9. In Examples 61 to 63 and 65

TABLE 8

| Example No. | Catalyst (5 mol. % to DPO) | Hal-Comp. | DPO (mmol) | Tem. (°C.) | Time (hr.) | DPO Con. (%) | DPC Sel. (%) | DPC Yield (%) |
|---|---|---|---|---|---|---|---|---|
| Ex.47 | Ph$_3$P=O | AlCl$_3$ | 24.8 | 270 | 3 | 53.5 | 94.0 | 50.3 |
| Ex.48 | Ph$_3$P=O | SOCl$_2$ | 20.7 | 255 | 3 | 88.2 | 86.5 | 76.3 |
| Ex.49 | Ph$_3$P=O | CCl$_4$ | 20.7 | 255 | 3 | 37.0 | 99.3 | 36.7 |
| Ex.50 | Ph$_3$P=O | C$_6$H$_5$CCl$_3$ | 20.7 | 255 | 3 | 98.4 | 81.9 | 80.6 |
| Ex.51 | Ph$_3$P=O* | Br-xylene | 20.7 | 255 | 3 | 93.6 | 60.3 | 56.4 |
| Ex.52 | Ph$_3$P=O | (COCl)$_2$ | 20.7 | 255 | 3 | 98.2 | 99.1 | 97.3 |
| Ex.53 | Ph$_3$P=O | C$_6$H$_5$COCl | 20.7 | 255 | 3 | 97.9 | 85.8 | 84.0 |
| Ex.54 | Ph$_3$P=O | p-tolu-Cl | 20.7 | 255 | 3 | 93.4 | 86.1 | 80.4 |
| Ex.55 | Ph$_3$P=O | C$_{10}$H$_7$SO$_2$Cl | 20.7 | 255 | 3 | 67.4 | 76.6 | 51.6 | to 67, a halogen atom-containing compound was added as set forth in Table 9.

The reaction conditions and results are set forth in Table 9.

solution, an aqueous solution of 6.76 g of acetic acid and 7.77 g of potassium carbonate in 25 mL of water was dropwise added under stirring for 4 hours. The mixture was then stirred for 2 hours, and the produced precipitate was

TABLE 9

| Example No. | Catalyst (mol. % to DPO) | Hal-Comp. (ratio) | DPO (mmol) | Tem. (°C.) | Time (hr.) | DPO Con. (%) | DPC Sel. (%) | DPC Yield (%) |
|---|---|---|---|---|---|---|---|---|
| Ex.56 | Ph$_4$P.Cl (0.1) | — | 20.7 | 280 | 2 | 84.4 | 99.0 | 83.6 |
| Ex.57 | Ph$_4$P.Cl (0.1) | CHCl$_3$ (5.5) | 20.8 | 280 | 2 | 94.0 | 99.0 | 93.1 |
| Ex.58 | Ph$_4$P.Cl (0.1) | ClCOOC$_6$H$_5$ (10) | 20.7 | 280 | 2 | 91.9 | 99.0 | 90.1 |
| Ex.59 | Ph$_4$P.Cl (0.1) | PCl$_5$ (8.1) | 20.7 | 280 | 2 | 95.4 | 99.0 | 94.4 |
| Ex.60 | Ph$_4$P.Br (0.5) | — | 20.7 | 260 | 1 | 13.0 | 77.0 | 10.0 |
| Ex.61 | Ph$_4$P.Br (0.5) | CHCl$_3$ (1.2) | 20.7 | 260 | 1 | 85.0 | 95.0 | 80.8 |
| Ex.62 | Ph$_4$P.Br (0.5) | (COCl)$_2$ (2.4) | 20.7 | 260 | 1 | 86.0 | 95.0 | 81.7 |
| Ex.63 | Ph$_4$P.Br (0.5) | HCl (300) | 20.7 | 260 | 1 | 80.9 | 96.0 | 77.7 |
| Ex.64 | Ph$_4$P.I (0.7) | — | 20.7 | 260 | 1 | 7.0 | 65.0 | 4.6 |
| Ex.65 | Ph$_4$P.I (0.7) | (COCl)$_2$ (1.1) | 20.7 | 260 | 1 | 84.0 | 84.0 | 70.6 |
| Ex.66 | Ph$_4$P.SCN (0.5) | (COCl)$_2$ (1.1) | 20.7 | 260 | 3 | 99.0 | 99.0 | 98.0 |
| Ex.67 | Ph$_4$P.CF$_3$CO$_2$ (0.5) | (COCl)$_2$ (1.1) | 20.7 | 260 | 3 | 99.0 | 99.0 | 98.0 |

Remarks:

The amount of Hal-Comp. (i.e., halogen atom-containing compound) is indicated in terms of ratio per the amount of the catalyst.

Ph$_4$P.SCN: tetraphenylphosphonium thiocyanide

Ph$_4$P.CF$_3$CO$_2$: tetraphenylphosphonium trifluoroacetate

EXAMPLE 68

The decarbonylation reaction was repeated in the manner as described in Example 22, except that tetraphenylphosphonium chloride was replaced with phenoxytriphenylphosphonium chloride (5 mol. % to DPD). The phenoxytriphenylphosphonium chloride was prepared by the known process (Liebigs Ann. Chem., 1975, 406).

It was confirmed that the conversion ratio of diphenyl oxalate was 97.6%, the selectivity was 91.4%, and the yield was 89.2%.

EXAMPLE 69

The decarbonylation reaction was repeated in the manner as described in Example 1, except that diphenyl oxalate was replaced with 1.30 g (4.18 mmol) of bis(4-chlorophenyl) oxalate, tetraphenylphosphonium chloride was employed in an amount of 5 mol. % based on the bis(4-chlorophenyl) oxalate, and the reaction time was changed to 20 minutes, to obtain 1.13 g (3.99 mmol) of bis(4-chlorophenyl) carbonate.

It was confirmed that the conversion ratio of bis(4-chlorophenyl) oxalate was 96.5%, the selectivity was 99.0%, and the yield was 95.5%.

Reference Example 4
Synthesis of phenyl chloroglyoxylate

In a 1,000 mL-volume three-necked flask, 27.3 g of diphenyl oxalate was dissolved in 600 mL of acetone. In the collected on a filter by suction. The collected precipitate was washed with acetone and dried under reduced pressure to give 19.9 g of potassium phenyl oxalate. These procedures were performed at room temperature.

The 18.99 g of the potassium salt was placed in a 100 mL-volume egg-plant type flask. In the flask placed in a water bath kept at 20° C., 16.58 g of thionyl chloride was dropwise added for 30 minutes. The temperature of the water bath was then raised to 90° C., and the reaction mixture was stirred for one hour.

After the reaction was complete, excessive thionyl chloride was distilled off, and the subsequent distillation under reduced pressure gave 14.5 g of phenyl chloroglyoxylate.

EXAMPLE 70
Preparation of Phenyl Chloroformate

In a 50 mL-volume glass flask equipped with a thermometer, a stirrer and a reflux condenser, 1.588 mmol. of phenyl chloroglyoxylate (PCG) was placed. To the PCG was added tetraphenylphosphonium chloride (Ph$_4$P.Cl) in an amount of 3.6 mol. % per the amount of PCG. The mixture was heated to 250° C. under stirring at an atmospheric pressure. The mixture was further stirred for 5 minutes at the same temperature to perform decarbonylation reaction, while the produced carbon monoxide was removed from the reaction mixture.

After the reaction was complete, the reaction mixture was cooled to room temperature and analyzed by gas chromatography. It was confirmed that the conversion ratio of phenyl chloroglyoxylate was 99.8%, and the selectivity to phenyl chloroformate (PCF) was 75.8%.

EXAMPLE 71
Preparation of Phenyl Chloroformate

The decarbonylation reaction of phenyl chloroglyoxylate (PCG) was repeated in the manner as described in Example 70, except that the amounts of tetraphenylphosphonium chloride and phenyl chloroglyoxylate were changed as set forth in Table 10, and that 7.0 g of diphenyl ether was employed as a reaction solvent. The results are also set forth in Table 10.

EXAMPLE 72
Preparation of Phenyl Chloroformate

The decarbonylation reaction of phenyl chloroglyoxylate (PCG) was repeated in the manner as described in Example 70, except that the amount of tetraphenylphosphonium chloride and phenyl chloroglyoxylate, the reaction temperature, and the reaction period were changed as set forth in Table 10. The results are also set forth in Table 10.

EXAMPLES 73–75
Preparation of Phenyl Chloroformate

The decarbonylation reaction of phenyl chloroglyoxylate (PCG) was repeated in the manner as described in Example 70, except that the tetraphenylphosphonium chloride was replaced with 3.4 mol. % of triphenylphosphine ($Ph_3P$), 3.2 mol. % of triphenylphosphine oxide ($Ph_3P$=O), or 3.7 mol. % of tetraphenylphosphonium hydrogen dichloride ($Ph_4P \cdot HCl_2$), and that the amount of phenyl chloroglyoxylate and the reaction period were changed as set forth in Table 10. The results are also set forth in Table 10.

Comparison Example 4
Preparation of Phenyl Chloroformate

The decarbonylation reaction of phenyl chloroglyoxylate (PCG) was repeated in the manner as described in Example 70, except that the tetraphenylphosphonium chloride was not employed and the amount of phenyl chloroglyoxylate was changed as set forth in Table 10. The results are also set forth in Table 10.

TABLE 10

| Example No. | Catalyst (mol. % to PCG) | PCG (mmol) | Tem. (°C.) | Time (hr.) | PCG Con. (%) | PCF Sel. (%) |
|---|---|---|---|---|---|---|
| Ex.70 | $Ph_4P \cdot Cl$(3.6) | 1.588 | 250 | 5 | 99.8 | 75.8 |
| Ex.71 | $Ph_4P \cdot Cl$(3.5) | 1.690 | 250* | 5 | 99.0 | 76.3 |
| Ex.72 | $Ph_4P \cdot Cl$(1.0) | 1.649 | 270 | 2.5 | 91.8 | 78.2 |
| Ex.73 | $Ph_3P$(3.4) | 1.595 | 250 | 3 | 95.5 | 82.7 |
| Ex.74 | $Ph_2P$=O(3.2) | 1.592 | 250 | 3 | 95.2 | 79.2 |
| Ex.75 | $Ph_4P \cdot HCl_2$(3.7) | 1.571 | 250 | 3 | 96.7 | 73.6 |
| Com.Ex.4 | — | 1.719 | 250 | 5 | 2.3 | 38.4 |

Remarks:
The reaction of Example 71 was performed in a solvent.

EXAMPLES 76–77
Preparations of 4-Methylphenyl Chloroformate and 4-Chlorophenyl Chloroformate The decarbonylation reaction was repeated in the manner as described in Example 70, except that the amount of tetraphenylphosphonium chloride was changed as set forth in Table 11, and that the phenyl chloroglyoxylate was replaced with 1.492 mmol. of 4-methylphenyl chloroglyoxylate (4-Me—PCG), or 1.399 mmol. of 4-chlorophenyl chloroglyoxylate (4-Cl—PCG). The results are also set forth in Table 11.

EXAMPLE 78
Preparation of 4-Methoxyphenyl Chloroformate

The decarbonylation reaction was repeated in the manner as described in Example 70, except that the amount of tetraphenylphosphonium chloride was changed as set forth in Table 11, that the phenyl chloroglyoxylate was replaced with 1.396 mmol. of 4-methoxyphenyl chloroglyoxylate (4-MeO—PCG), and that the reaction temperature and reaction period were changed as set forth in Table 11. The results are also set forth in Table 11.

TABLE 11

| Example No. | $Ph_4P \cdot Cl$ (mol % to PCG) | PCG (mmol) | Tem. (°C.) | Time (hr.) | PCG Con. (%) | PCF Sel. (%) |
|---|---|---|---|---|---|---|
| Ex.76 | (2.9) | 4-Me-PCG(1.492) | 250 | 5 | 99.8 | 75.9 |
| Ex.77 | (3.0) | 4-Cl-PCG(1.399) | 250 | 5 | 99.0 | 76.3 |
| Ex.78 | (2.9) | 4-MeO-PCG(1.396) | 270 | 2.5 | 91.8 | 78.2 |

Reference Example 5
Synthesis of phenyl phenylglyoxylate

In a 50 mL-volume flask, 12.2 g of phenyl glyoxylic acid was placed, and then 9.26 g of dichloromethyl methyl ether was dropwise added at room temperature. The mixture was stirred at room temperature for 1 hour. The reaction mixture was placed under reduced pressure (62° C./2 torr) to give 13.4 g of phenylglyoxylic acid chloride. The obtained phenylglyoxylic acid chloride was dropwise added to a mixture of 7.86 g of phenol, 7.26 g of pyridine and 10 mL of toluene. The resulting mixture was stirred at 50° C. for 2 hours.

After the stirring was complete, the reaction mixture was subjected to extraction with methylene chloride. The extract solution was washed successively with water and hydrochloric acid. After methylene chloride was distilled off, the extract was distilled at 145° C. and 3 torr to give 15.3 g of phenyl phenylglyoxylate.

EXAMPLE 79
Preparation of Phenyl Benzoate

In a 50 mL-volume glass flask equipped with a thermometer and a reflux condenser, 10.3 mmol. of phenyl phenylglyoxylate (PPG) was placed. To the PPG were added tetraphenylphosphonium chloride ($Ph_4P \cdot Cl$) in an amount of 1.0 mol. % per the amount of PPG and chloroform in an amount which was equimolar to ($Ph_4P \cdot Cl$). The mixture was heated to 250° C. under stirring. The mixture was further stirred for 1 hour at the same temperature and at an atmospheric pressure to perform decarbonylation reaction, while the produced carbon monoxide was removed from the reaction mixture.

After the reaction was complete, the reaction mixture was cooled to room temperature and analyzed by gas chromatography. It was confirmed that the conversion ratio of phenyl phenylglyoxylate was 99.3%, and the selectivity to phenyl benzoate (PB) was 87.4%.

EXAMPLES 80 TO 82
Preparation of Phenyl Benzoate

The decarbonylation reaction of phenyl phenylglyoxylate (PPG) was repeated in the manner as described in Example 79, except that the organic phosphorus compound set forth in Table 12 was employed and the amount of chloroform was changed as set forth in Table 12. The results are also set forth in Table 12.

Comparison Example 5
Preparation of Phenyl Benzoate

The decarbonylation reaction of phenyl phenylglyoxylate (PPG) was repeated in the manner as described in Example 79, except that neither tetraphenylphosphonium chloride nor chloroform was employed. The results are also set forth in Table 12.

TABLE 12

| Example No. | Catalyst (mol. % to PPG) | CHCl$_3$ (mol. ratio) | PPG (mmol) | Tem. (°C.) | Time (hr.) | PPG Con. (%) | PB Sel. (%) |
|---|---|---|---|---|---|---|---|
| Ex.79 | Ph$_4$P.Cl (1.0) | 1.0 | 10.3 | 250 | 1 | 99.3 | 87.4 |
| Ex.80 | Ph$_3$P (10) | 1.8 | 10.3 | 250 | 2 | 36.6 | 66.4 |
| Ex.81 | Ph$_3$P=O (10) | 2.0 | 10.3 | 250 | 2 | 29.2 | 61.6 |
| Ex.82 | Ph$_3$P.Cl$_2$ (10) | — | 10.3 | 250 | 2 | 32.4 | 59.8 |
| Con.5 | — | — | 10.3 | 250 | 1 | 16.2 | 17.0 |

EXAMPLE 83
Preparation of Phenyl 4-Chlorobenzoate

The decarbonylation reaction of Example 79 was repeated except that phenyl phenylglyoxylate (PPG) was replaced with 4-chlorophenyl phenylglyoxylate (4-CPPG), and that the amounts of tetraphenylphosphonium chloride and chloroform were changed as set forth in Table 13. The results are set forth in Table 13.

EXAMPLES 84 TO 86
Preparation of Phenyl 4-Chlorobenzoate

The decarbonylation reaction of Example 83 was repeated except that tetraphenylphosphonium chloride was replaced with that set forth in Table 13 and that the amount of chloroform and the reaction period were changed as set forth in Table 13. The results are set forth in Table 13.

Comparison Example 6
Preparation of Phenyl 4-Chlorobenzoate

The decarbonylation reaction of Example 83 was repeated except that neither tetraphenylphosphonium chloride nor chloroform was employed. The results are set forth in Table 13.

TABLE 13

| Example No. | Catalyst (mol. % to 4-CPPG) | CHCl$_3$ (mol. ratio) | 4-CPPG (mmol) | Tem. (°C.) | Time (hr.) | 4-CPPG Con. (%) | 4-CPB Sel. (%) |
|---|---|---|---|---|---|---|---|
| Ex.83 | Ph$_4$P.Cl(1.4) | 3.9 | 1.126 | 250 | 1 | 96.5 | 87.0 |
| Ex.84 | Ph$_3$P (10) | 2.3 | 1.991 | 250 | 2 | 84.4 | 86.3 |
| Ex.85 | Ph$_3$P.Cl$_2$ (10) | — | 1.136 | 250 | 1 | 54.2 | 84.1 |
| Ex.86 | Ph$_3$P.Cl$_2$(3.3) | 3.3 | 1.136 | 250 | 1 | 34.7 | 70.4 |
| Con.6 | — | — | 1.089 | 250 | 1 | 9.5 | 0 |

Remark
4-CPB: 4-Chlorophenyl benzoate

EXAMPLE 87
Preparation of Dimethyl Carbonate

In a 10 mL-volume autoclave, dimethyl oxalate (1.24 mmol.) and tetraphenylphosphonium chloride (0.062 mmol., 5 mol. % per the amount of dimethyl oxalate) were heated to 220° C. and kept at the temperature for 3 hours so as to perform decarbonylation reaction.

After the reaction was complete, the reaction mixture was cooled to room temperature and analyzed by gas chromatography. It was confirmed that the conversion ratio of dimethyl oxalate (DMO) was 100%, and the yield of dimethyl carbonate (DMC) was 93.0%.

EXAMPLES 88 TO 90
Preparation of Dimethyl Carbonate

The decarbonylation reaction of dimethyl oxalate (DMO) was repeated in the manner as described in Example 87, except that the amounts of dimethyl oxalate and tetraphenylphosphonium chloride were changed as set forth in Table 14, and that the reaction temperature was changed as set forth in Table 14. The results are also set forth in Table 14.

EXAMPLE 91
Preparation of Dimethyl Carbonate

The decarbonylation reaction of dimethyl oxalate (DMO) was repeated in the manner as described in Example 87, except that tetraphenylphosphonium chloride was replaced with 0.0655 mmol. of tetraphenylphosphonium phenoxide-phenol complex (prepared in the manner as described in U.S. Pat. No. 4,340,761) and the amount of dimethyl oxalate was changed as set forth in Table 14.

EXAMPLE 92
Preparation of Dimethyl Carbonate

The decarbonylation reaction of dimethyl oxalate (DMO) was repeated in the manner as described in Example 87, except that tetraphenylphosphonium chloride was replaced with 0.1005 mmol. of tetraphenylphosphonium benzoate and the amount of dimethyl oxalate was changed as set forth in Table 14.

The tetraphenylphosphonium benzoate was prepared in the following manner.

In a 100 mL-volume egg plant type flask, tetraphenylphosphonium chloride (5.00 g) and potassium benzoate (2.20 g) were dissolved in methanol (15 mL), and the resulting solution was stirred at 65° C. for 5 hours. To the stirred mixture was dropwise added toluene (15 mL) at the same temperature for 0.5 hour. The solution was cooled to room temperature, and further stirred for one hour. After the stirring was complete, the mixture was filtered to remove the produced precipitate, and the filtrate was placed under reduced pressure to give a concentrated slurry. To the slurry was added acetone (40 mL), and the mixture was stirred. The produced insolubles were removed by filtration, and the filtrate was stirred after addition of toluene (180 mL) and ether (80 mL). The produced precipitate was collected by filtration and washed with toluene. The precipitate was recrystallized from acetone and dried under reduced pressure at 80°–100° C. for 2.5 hours, to obtain 1.78 g of tetraphenylphosphonium benzoate. From the filtrate, 0.48 g of tetraphenylphosphonium benzoate was obtained after concentration and recrystallization. Yield (total): 38%, m.p.: 129°–131° C., analysis: C 80.63%, H 5.48% (calculated: C 80.85%, H 5.47%).

EXAMPLE 93
Preparation of Dimethyl Carbonate

The decarbonylation reaction of dimethyl oxalate (DMO) was repeated in the manner as described in Example 87, except that tetraphenylphosphonium chloride was replaced with 0.0995 mmol. of tetraphenylphosphonium 2-thionaphthoxide and the amount of dimethyl oxalate was changed as set forth in Table 14.

The tetraphenylphosphonium 2-thionaphthoxide was prepared in the following manner.

In a 100 mL-volume egg plant type flask, 2-naphthalenethiol (1.71 g) and 1M aqueous sodium hydroxide solution (10.6 mL) were mixed, and to the mixture was added ethanol (20 mL). The resulting mixture was placed under reduced pressure (30 mmHg) at 60° C. to distill off water and ethanol. To the residue was added ethanol (20 mL) and the mixture was placed under reduced pressure in the same conditions to further distill off water by azeotropic distillation. The azeotropic distillation was twice performed. To the residue was further added a mixture of ethanol (20 mL) and toluene (10 mL), and placed under reduced pressure in the same conditions to further distill off water by azeotropic distillation.

The residue was dried at 150° C. and placed in a mixture of ethanol (20 mL) and toluene (10 mL) at 60° C. To the resulting solution was added tetraphenylphosphonium chloride (4.00 g). The mixture was stirred until the temperature of the mixture reached to room temperature, and the mixture was further stirred for one hour. After the stirring was complete, toluene (10 mL) was added to the mixture, and the produced precipitate was removed by filtration. The filtrate was concentrated under reduced pressure. The yield was dissolved in a heated mixture of ethanol (1 mL) and tetrahydrofuran (20 mL). To the resulting solution was further added 20 mL of tetrahydrofuran, and the mixture was cooled to room temperature. Thus produced precipitate was collected by filtration and washed with tetrahydrofuran. The washed precipitate was dried under reduced pressure at 85° C. for 1 hour, to obtain tetraphenylphosphonium 2-thionaphthoxide (3.00 g, yield: 57%, m.p.: 143°–147° C., analysis: C 81.92%, H 5.46%, calculated: C 81.90%, H 5.46%). These procedures were all conducted in a stream of argon.

TABLE 14

| Example No. | Catalyst (mol. % to DMO) | DMO (mmol) | Tem. (°C.) | Time (hr.) | DMO Con. (%) | DMC Yield (%) |
|---|---|---|---|---|---|---|
| Ex.87 | Ph$_4$P.Cl(5) | 1.24 | 220 | 3 | 100 | 93.0 |
| Ex.88 | Ph$_4$P.Cl(5) | 1.37 | 200 | 3 | 100 | 95.0 |
| Ex.89 | Ph$_4$P.Cl(1.5) | 1.31 | 200 | 3 | 100 | 95.0 |
| Ex.90 | Ph$_4$P.Cl(5) | 1.37 | 180 | 3 | 100 | 91.8 |
| Ex.91 | Ph$_4$P(OPh).PhOH(5) | 1.31 | 220 | 3 | 100 | 84.1 |
| Ex.92 | Ph$_4$P(OCOC$_6$H$_5$)(5) | 2.01 | 100 | 3 | 100 | 85.6 |
| Ex.93 | Ph$_4$P(SC$_{10}$H$_7$)(5) | 1.90 | 100 | 3 | 100 | 82.7 |

EXAMPLE 94

Preparation of Phenyl 2-Thiophenecarboxylate

In a 50 mL-volume glass flask equipped with a thermometer, a stirrer and a reflux condenser, a mixture of 1.32 mmol. of phenyl 2-thienylglyoxylate, 0.023 mmol. of tetraphenylphosphonium chloride (Ph$_4$P.Cl), and 0.23 mmol. of chloroform was heated to 250° C. at an atmospheric pressure. At that temperature, the mixture was subjected to decarbonylation reaction for one hour, while the produced carbon monoxide was removed.

After the reaction was complete, the reaction mixture was cooled to room temperature and analyzed by gas chromatography. It was confirmed that the conversion ratio of phenyl 2-thienylglyoxylate was 73.5%, and the selectivity to phenyl 2-thiophenecarboxylate was 55.6%. The phenyl 2-thienylglyoxylate was prepared by the process described in Synthesis, 1975, 163.

Comparison Example 7

Preparation of Phenyl 2-Thiophenecarboxylate

The decarbonylation reaction of Example 94 was repeated except that neither tetraphenylphosphonium chloride nor chloroform was employed. The conversion ratio of phenyl 2-thienylglyoxylate was 10.6%, and the selectivity to phenyl 2-thiophenecarboxylate was 18.0%.

EXAMPLE 95

Preparation of Phenyl 2-Furancarboxylate

In a 50 mL-volume glass flask equipped with a thermometer, a stirrer and a reflux condenser, a mixture of 1.45 mmol. of phenyl 2-furylglyoxylate, 0.017 mmol. of tetraphenylphosphonium chloride (Ph$_4$P.Cl), and 0.63 mmol. of chloroform was heated to 250° C. at an atmospheric pressure. At that temperature, the mixture was subjected to decarbonylation reaction for one hour, while the produced carbon monoxide was removed.

After the reaction was complete, the reaction mixture was cooled to room temperature and analyzed by gas chromatography. It was confirmed that the conversion ratio of phenyl 2-furylglyoxylate was 67.4%, and the selectivity to phenyl 2-furancarboxylate was 27.6%. The phenyl 2-furylglyoxylate was prepared by the process described in Synthesis, 1975, 163.

Comparison Example 8

Preparation of Phenyl 2-Furancarboxylate

The decarbonylation reaction of Example 95 was repeated except that neither tetraphenylphosphonium chloride nor chloroform was employed. The conversion ratio of phenyl 2-furylglyoxylate was 8.1%, and the selectivity to phenyl 2-furylcarboxylate was 0%.

What is claimed is:

1. A process for releasing carbon monoxide from a compound containing a moiety having the formula:

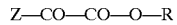

in which Z is an aryl group, a halogen atom, a heterocyclic group, an aryloxy group, or an alkoxy group, and R is an aryl group or an alkyl group in its molecular structure which comprises heating the compound in the presence of an organic phosphorus compound having a trivalent or pentavalent phosphorus atom and at least one carbon-phosphorus bonding.

2. The process of claim 1, wherein the organic phosphorus compound is a phosphonium salt, a phosphine, a phosphine dihalide, or a phosphine oxide.

3. The process of claim 1, wherein the organic phosphorus compound is a tetraarylphosphonium salt, a triarylphosphine, a triarylphosphine dihalide, or a triarylphosphine oxide.

4. The process of claim 1, wherein the organic phosphorus compound is a tetraarylphosphonium halide, a tetraarylphosphonium hydrogen dihalide, or a triarylphosphine dihalide.

5. A process for releasing carbon monoxide from a compound containing a moiety having the formula:

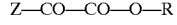

in which Z is an aryl group, a halogen atom, a heterocyclic group, an aryloxy group, or an alkoxy group, and R is an aryl group or an alkyl group in its molecular structure which comprises heating the compound in the presence of an organic phosphorus compound having a trivalent or pentavalent phosphorus atom and at least one carbon-phosphorus bonding and a halogen atom-containing compound.

6. The process of claim 5, wherein the organic phosphorus compound is a phosphonium salt, a phosphine, a phosphine dihalide, or a phosphine oxide.

7. The process of claim 5, wherein the organic phosphorus compound is a tetraarylphosphonium salt, a triarylphosphine, a triarylphosphine dihalide, or a triarylphosphine oxide.

8. The process of claim 5, wherein the organic phosphorus compound is a tetraarylphosphonium halide, a tetraarylphosphonium hydrogen dihalide, or a triarylphosphine dihalide.

9. The process of claim 5, wherein the halogen atom-containing compound is an organic or inorganic halide compound.

10. The process of claim 5, wherein the halogen atom-containing compound is a compound selected from the group consisting of halides of aluminum, halides of metals belonging to the platinum group, halides of phosphorus, hydrogen halides, halides of sulfur, and halogens.

11. The process of claim 5, wherein the halogen atom-containing compound is an organic compound having a C—Hal bonding, Hal meaning a halogen atom, a C—Si—Hal bonding, a C(O)—Hal bonding, or a C—S(O)$_2$—Hal bonding.

12. The process of claim 5, wherein the halogen atom-containing compound is a chlorine atom-containing compound.

* * * * *